United States Patent [19]

Kleemann et al.

[11] 4,436,910

[45] Mar. 13, 1984

[54] PROCESS FOR THE PRODUCTION OF AQUEOUS SOLUTIONS OF SODIUM SALTS OF α-AMINO CARBOXYLIC ACIDS

[75] Inventors: Axel Kleemann, Hanau; Bernd Lehmann, Freigericht; Jürgen Martens, Alzenau, all of Fed. Rep. of Germany

[73] Assignee: Degussa Aktiengesellschaft, Frankfurt am Main, Fed. Rep. of Germany

[21] Appl. No.: 347,477

[22] Filed: Feb. 10, 1982

[30] Foreign Application Priority Data

Feb. 12, 1981 [DE] Fed. Rep. of Germany ....... 3105008

[51] Int. Cl.³ .................. C07D 211/60; C07D 207/16
[52] U.S. Cl. ..................................... 546/245; 548/499; 548/535; 562/443; 562/444; 562/445; 562/446; 562/503; 562/507; 562/557; 562/571; 562/573; 562/574; 562/575
[58] Field of Search ............... 562/443, 444, 445, 446, 562/503, 507, 557, 571, 573, 574, 575; 546/245; 548/499, 535

[56] References Cited

U.S. PATENT DOCUMENTS 3,790,599  2/1974  Zundel ............................... 548/499

OTHER PUBLICATIONS

*Chemical Abstracts,* 92:22055y (1980) [Japan Kokai 79, 88, 217, Kondo et al., 7/13/79].

*Primary Examiner*—Richard A. Schwartz
*Attorney, Agent, or Firm*—Cushman, Darby & Cushman

[57] ABSTRACT

Aqueous solutions of sodium salts of α-aminocarboxylic acids practically free of foreign salts are produced by saponifying the corresponding hydantoin at a temperature between 110° C. and 180° C. with a mixture, in each case based on the hydantoin, of 1 equivalent of sodium hydroxide and 2 equivalents of calcium oxide or hydroxide, separating off the precipitated calcium carbonate after the end of the saponification and concentrating the aqueous sodium salt solution remaining to drive off the ammonia contained therein.

9 Claims, No Drawings

PROCESS FOR THE PRODUCTION OF AQUEOUS SOLUTIONS OF SODIUM SALTS OF α-AMINO CARBOXYLIC ACIDS

BACKGROUND OF THE INVENTION

The invention is directed to a process for the production of aqueous solutions of sodium salts of α-aminocarboxylic acids practically free from foreign salts by alkaline saponification of the corresponding hydantoin at a temperature between 110° and 180° C.

It has been known for over 70 years to produce the various α-aminocarboxylic acids by alkaline saponification of the corresponding hydantoins at a temperature between 110° and 180° C. As saponification agent there generally is employed sodium hydroxide and/or sodium carbonate. In the saponification there is then formed an aqueous solution which besides the sodium salt of the α-aminocarboxylic acid necessarily also contains a more or less large amount of one half to one mole per mole of α-aminocarboxylic acid. The isolation of the α-aminocarboxylic acid from this solution then frequently is carried out by adsorption on an acid ion exchanger and subsequent elution with a suitable eluting agent.

However, in this type of working up the content of sodium carbonate in the solution is disturbing because it reduces considerably the capacity of the ion exchange plant. Therefore it is desirable to carry out the saponification of the hydantoin in such a manner that the saponification mixture besides the α-aminocarboxylic acid salt contains as low as possible amounts of dissolved foreign salts.

BRIEF DESCRIPTION OF THE INVENTION

The process of the invention is characterized by employing as the saponification agent a mixture, in each case based on the hydantoin employed, of 1 equivalent of sodium hydroxide and 2 equivalents of calcium oxide or hydroxide, after the end of the saponification separating off the precipitated calcium carbonate and concentrating the aqueous sodium salt solution remaining to drive off the ammonia contained therein.

Surprisingly the separated calcium carbonate is practically free from the α-aminocarboxylic acid formed and salts of this acid so that the aqueous solution remaining contains this α-aminocarboxylic acid in high yield in the form of its sodium salt. An additional advantage of the process of the invention is that the precipitated calcium carbonate apparently adsorbs specific byproducts and through this exerts a purification action on the aqueous solution remaining.

Apart from the choice of saponification agent the saponification of the hydantoin is carried out in known manner. The saponification takes place at a temperature of 110° to 180° C., preferably between 120° and 150° C., and in the simplest case at the pressure which necessarily results at the chosen saponification temperature.

In the process of the invention there can be employed any hydantoin, for example those of the formula

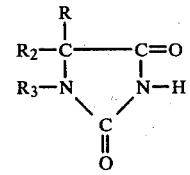

where $R_1$ and $R_2$ are the same or different and are hydrogen a straight or branched chain 1 to 20 carbon atom alkyl group, e.g., methyl, ethyl, propyl, isobutyl, t-butyl, amyl, hexyl, octyl, decyl, hexadecyl, eicosamyl, which alkyl group can be substituted, or a straight or branched chain alkenyl group with 2 to 10 carbon atoms, e.g. vinyl, allyl, methallyl, crotyl, 9-decenyl, a straight or branched chain alkinyl group with 2 to 6 carbon atoms, e.g. ethinyl, propinyl, 2-hexinyl, a cycloalkyl group or cycloalkenyl group with 3 to 8 carbon atoms, e.g. cyclopropyl, cyclopentyl, cyclohexyl, cyclooctyl, cyclopentenyl, cyclohexenyl, cyclooctenyl or a phenyl group which in a given case can be substituted e.g., where the substituent is hydroxy, halogen, alkoxy or phenoxy, $R_3$ is hydrogen or an alkyl group with 1 to 10 carbon atoms, e.g. methyl, ethyl, propyl, butyl, isobutyl, amyl, hexyl, octyl or decyl or $R_1$ and $R_2$ or $R_2$ and $R_3$ together are an alkylene group having 3 to 5 carbon atoms, e.g. trimethylene, tetramethylene, pentamethylene. If $R_1$ and/or $R_2$ is a substituted alkyl group having 1 to 20 carbon atoms as substituents there can be used for example phenyl, halophenyl, e.g. 4-fluorophenyl, 4-chlorophenyl, hydroxyphenyl, e.g. 4-hydroxyphenyl, 3-hydroxyphenyl, 3,4-dihydroxyphenyl, alkoxyphenyl, e.g. 3-methoxyphenyl, 4-ethoxyphenyl, 3,4-dimethoxyphenyl, 3-indolyl, sulfur functions, e.g. 4-hydantoyl-2',3'-dithiobutyl, carboxy groups, e.g. carboxymethyl, carboxyethyl, carboxypropyl, carboxybutyl, carboxamide groups, e.g. carboxamidomethyl, carboxamidoethyl, halogen, e.g. fluorine, chlorine, bromine and iodine (especially fluorine or chlorine), e.g. fluoromethyl, chloromethyl, bromomethyl, fluoroethyl, chloroethyl, chlorobutyl, chlorobutyl, fluorodecyl, fluoroeicosamyl, chloroeicosamyl, cycloalkyl group with 3 to 8 carbon atoms, e.g. cyclopropylmethyl, cyclohexylmethyl, cyclohexylethyl, or cycloalkenyl groups having 3 to 8 carbon atoms, e.g. cyclopentenylethyl or cyclohexylmethyl. If $R_1$ and/or $R_2$ is a substituted phenyl it can be for example a hydroxyphenyl group, e.g. 4-hydroxyphenyl, 3,4-dihydroxyphenyl or 3-hydroxyphenyl, a halophenyl groups, e.g. 4-chlorophenyl, 4-fluorophenyl, 4-bromophenyl, 2,4-dichlorophenyl, 2,4-difluorophenyl, a phenoxyphenyl group, e.g. 3-phenoxyphenyl, or alkoxyphenyl, e.g. 4-methoxyphenyl, 3,4-dimethoxyphenyl.

Examples of such hydantoins are the base material hydantoin, 5-methylhydantoin, 5-n-propylhydantoin, 5-i-propylhydantoin, 5-i-butylhydantoin, 5-sec.-butylhydantoin, 5-n-pentadecylhydantoin, 5-phenylhydantoin, 5-(4'-hydroxyphenyl)-hydantoin, 5-(4'-fluorophenyl)-hydantoin, 5-(3'-phenoxyphenyl)hydantoin, 5-benzyl-hydantoin, 5-(3',4'-dihydroxybenzyl)-hydantoin, 5-[indolyl-(3)-methyl]-hydantoin, 5-[4'-hydanto-5-yl-2',3'-dithia-butyl]-hydantoin, 5-carboxymethylhydantoin, 5-amidomethylhydantoin, 5-(2'-carboxyethyl)-hydantoin, 5-(2'-amidoethyl)-hydantoin, 5-fluormethylhydantoin, 5-chloromethylhydantoin, 5-cyclohexylhydantoin, 5-cyclopentylhydantoin, 5-(cyclohexylmethyl)-hydantoin, 5-[cyclohex-3-en-1-yl]- hydantoin, 5-[cyclohex-3-en-1-yl-methyl]hydantoin, 5-vinylhydantoin, 5-ethinylhydantoin, 5-(4'-methoxyphenylmethyl)-hydantoin, 5-(3',4'-dimethoxyphenylmethyl)-hydantoin, 5-(4'-hydroxybenzyl)-5-vinylhydantoin, 5-benzyl-5-ethinyl-hydantoin, 5,5-dimethylhydantoin, 5,5-tetramethylenhydantoin, 5,5-trimethylenhydantoin, 1,5-trimethylenhydantoin or 1,5-tetramethylenhydantoin.

Additional substituted hydantoins include 5-n-eicosamylhydantoin, 5,5-diethylhydantoin, 5-methyl-5-ethylhydantoin, 5-allylhydantoin, 5-methallylhydantoin, 5-decen-9-ylhydantoin, 5-hexinylhydantoin, 5-cyclooctylhydantoin, 5-cyclopropylhydantoin, 1-methylhydantoin, 1,5-dimethylhydantoin, 1,5,5-trimethylhydantoin, 1-ethylhydantoin, 1-butylhydantoin, 5,5-pentamethylenehydantoin, 5-fluoroethylhydantoin, 5-chloroethylhydantoin, 5-(4'-chlorophenyl)hydantoin, 5,5-diphenylhydantoin, 5-methyl-5-phenylhydantoin, or 5-(3',4'-dimethoxyphenyl)hydantoin.

The amount of 1 equivalent of sodium hydroxide and 2 equivalents of calcium oxide or hydroxide is exactly what is required for the saponification of the hydantoin ring. If the hydantoin to be saponified contains more than one hydantoin ring, e.g. in the case of the dihydantoin of cystine naturally there must be employed the multiple amount. If the hydantoin to be saponified contains a carboxyl or carboxamide group then there must be employed a further equivalent of sodium hydroxide. Finally if there is employed a crude aqueous solution of a hydantoin which still contains excess of ammonium carbonate from the hydantoin synthesis, then it is necessary either to drive off this ammonium carbonate before the saponification reaction by a treatment with steam or, which is simpler, to add an additional amount of calcium oxide or hydroxide equivalent to the content of carbonate ions.

After the end of the saponification and cooling the hydrolysis mixture the calcium carbonate is separated off by filtration or centrifugation. Through calcining it can be converted again into calcium oxide in the usual manner and this again employed in the saponification.

The aqueous solution remaining after the separation of the calcium carbonate then still contains at least a portion of the ammonia set free in the saponification of the hydantoin, which can be drawn off by simple concentration. There is obtained a practically pure solution of the desired α-aminocarboxylic acid.

The hydantoin can be employed in the process of the invention in the racemic D,L-form or in the form of D- or L-enantiomer.

The process of the invention is explained in more detail in the following examples. All percentages given are percent by weight.

The process can comprise, consist essentially of or consist of the stated steps with the recited materials.

EXAMPLE 1

25 grams (0.25 mole) of hydantoin, 18.5 grams (0.25 mole) of calcium hydroxide and 10 grams (0.25 mole) of sodium hydroxide were stirred in 150 ml of water in an autoclave for 4 hours at 140° C. After cooling to 50° C. the calcium carbonate which separated out was filtered off. The residue on the filter was washed with water and dried. It weighed 25 grams and consisted of 99.5 weight percent of calcium carbonate. The filtrate and wash water were combined and concentrated to drive off the ammonia contained therein. There was obtained a colorless solution which contained 23.5 grams (97% of theory) of the sodium salt of glycine. No calcium was detectable in this solution by complexometric titration.

EXAMPLE 2

The procedure was as in Example 1 but in place of hydantoin there were employed 32 grams (0.25 mole) of 5,5-dimethylhydantoin.

There was obtained a weakly yellow solution which contained 30.6 grams (98% of theory) of the sodium salt of α-aminoisobutyric acid.

EXAMPLE 3

The procedure was as in Example 1 but in place of hydantoin there were employed 47.5 grams (0.25 mole) of 5-benzylhydantoin.

There was obtained a weakly yellow solution which contained 44 grams (94% of theory) of the sodium salt of phenylalanine.

EXAMPLE 4

The procedure was as in Example 1 but in place of hydantoin there was employed 28.5 grams (0.25 mole) of 5-methylhydantoin.

There was obtained a solution which contained 26.5 grams (96% of theory) of the sodium salt of alanine.

EXAMPLES 5 TO 19

The procedure was as in Example 1 but in place of hydantoin there saponified in each case 0.25 mole of different hydantoin derivatives. The results are collected in the following table.

| Example | Hydantoin Derivatives Employed | Obtained: Sodium salt of | Yield (in % of Theory) |
|---|---|---|---|
| 5 | 5-phenylhydantoin | Phenylglycine | 91 |
| 6 | 5-i-butylhydantoin | Leucine | 95 |
| 7 | 5-(4'-hydroxyphenyl)-hydantoin | 4-hydroxyphenyl-glycine | 92 |
| 8 | 5-(Indolyl-3-methyl)-hydantoin | Tryptophani | 89 |
| 9 | 5-Fluormethyl-hydantoin | 3-Fluoroalanine | 95 |
| 10 | 5-Cyclohexyl-hydantoin | 2-Cyclohexylglycine | 96 |
| 11 | 5-(Cyclohexylmethyl)-hydantoin | 3-Cyclohexylalanine | 94 |
| 12 | 5-(4'-Hydroxybenzyl)-hydantoin | Tyrosine | 93 |
| 13 | 5-(3',4'-Dihydroxybenzyl)-hydantoin | 3,4-Dihydroxyphenylalanine | 93 |
| 14 | 5-(4'-Methoxybenzyl)-hydantoin | 4-Methoxyphenylalanine | 96 |
| 15 | 5-Vinylhydantoin | 2-Amino-vinylacetic acid | 91 |
| 16 | 5-Benzyl-5-ethinyl-hydantoin | α-Ethinyl-phenylalanine | 92 |
| 17 | 5,5-Trimethylene-hydantoin | 1-Aminocyclopentanecarboxylic acid | 96 |
| 18 | 1,5-Trimethylene-hydantoin | Proline | 95 |
| 19 | 1,5-Tetramethylene-hydantoin | Pipecolic acid | 95 |

EXAMPLE 20

23.7 Grams (0.15 mole) of 5-carboxymethylhydantoin, 11.1 grams (0.15 mole) of calcium hydroxide and 12 grams (0.30 mole) of sodium hydroxide were stirred in 150 ml of water in an autoclave for 4 hours at 140° C. After cooling to 50° C. the calcium carbonate which separated out was filtered of. The residue on the filter was washed with water and dried. The filtrate and the wash water were combined and concentrated to drive off the ammonia contained therein. The solution obtained contained according to the analysis in the aminoacid analyzer 25.5 grams (95% of theory) of the disodium slat of aspartic acid.

EXAMPLES 21 TO 23

The procedure was as described in Example 20 but in each case there was saponified 0.15 mole of a further derivative of hydantoin. The results are collected in the following table:

| Example | Hydantoin Derivative Employed | Obtained: Disodium salt of | Yield (in % of Theory) |
|---|---|---|---|
| 21 | 5-(Amidomethyl)-hydantoin | Asparatic acid | 94 |
| 22 | 5-(2'-Carboxyethyl)-hydantoin | Glutamic acid | 96 |
| 23 | 5-(2'-Amidoethyl)-hydantoin | Glutamic acid | 95 |

EXAMPLE 24

29 Grams (0.1 mole) of 5-(4'-hydanto-5-yl-2',3'-dithiabutyl)-hydantoin, 14.8 grams (0.2 mole) of calcium hydroxide and 8 grams (0.2 mole) of sodium hydroxide was stirred in 150 ml of water in an autoclave for 4 hours at 140° C. After cooling to 50° C. the calcium carbonate which separated out was filtered off. The filter residue was washed with water.

The filtrate and the wash water were combined and concentrated to drive off the ammonia contained therein.

The solution obtained contained 26.7 grams (94% of theory) of the disodium salt of cystine.

If the pH is adjusted to 5 with 16.6 ml of concentrated hydrochloric acid then cystine precipitates. After drying it weighed 22.5 grams.

The entire disclosure of German priority application P 3105008.5 is hereby incorporated by reference.

What is claimed is:

1. A process for the production of an aqueous solution of the sodium salt of an α-aminocarboxylic acid practically free from foreign salts comprising saponifying under alkaline conditions the corresponding hydantoin at a temperature between 110° and 180° C. employing based on the hydantoin 1 equivalent of sodium hydroxide and 2 equivalents of calcium oxide or hydroxide per hydantoin group, after the end of the saponification separating off the precipitated calcium carbonate and concentrating the remaining aqueous sodium salt solution to drive off the ammonia contained therein with the proviso that there is additionally employed 1 equivalent of sodium hydroxide for any carboxyl or carbamido group present in the hydantoin, the materials employed consisting essentially of the hydantoin, sodium hydroxide, calcium oxide or hydroxide and water.

2. A process according to claim 1 wherein the saponification of the hydantoin is carried out at 120° to 150° C.

3. A process according to claim 1 wherein the hydantoin employed has the formula

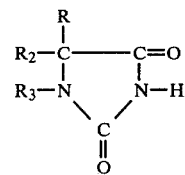

where $R_1$ and $R_2$ are (1) hydrogen, (2) 1 to 20 carbon atom alkyl, (3) substituted 1 to 20 carbon atom alkyl wherein the substituent is phenyl, hydroxyphenyl, alkoxyphenyl, halophenyl, indolyl, sulfur function, carboxy, carboxamido, halogen, cycloalkyl of 3 to 8 carbon atoms or cycloalkenyl of 3 to 8 carbon atoms, (4) 2 to 10 carbon atom alkenyl, (5) 2 to 6 carbon atom alkinyl, (6) 3 to 8 carbon atom cycloalkyl, (7) 3 to 8 carbon atom cycloalkenyl, (8) phenyl or (9) substituted phenyl wherein the substituent is hydroxy, halogen, alkoxy, phenoxy, or $R_1$ and $R_2$ together or $R_2$ and $R_3$ together are an alkylene group having 3 to 5 carbon atoms and $R_3$ is hydrogen or a 1 to 10 carbon atom alkyl.

4. A process according to claim 3 wherein when one of $R_1$ and $R_2$ is a sulfur function substituted it is 4-hydanto-5-yl-2,3-dithiabutyl and the other of $R_1$ and $R_2$ is hydrogen.

5. A process according to claim 4 wherein $R_2$ is hydrogen.

6. A process according to claim 4 wherein $R_1$ and $R_2$ together are 3 to 5 carbon atom alkylene and $R_3$ is hydrogen or $R_2$ and $R_3$ together are 3 to 5 carbon atom alkylene and $R_1$ is hydrogen.

7. A process according to claim 4 wherein the starting hydantoin compound is hydantoin per se, 5,5-dimethylhydantoin, 5-benzylhydantoin, 5-methylhydantoin, 5-phenylhydantoin, 5-isobutylhydantoin, 5-(4'-hydroxyphenyl)-hydantoin, 5-(indolyl-3-methyl)-hydantoin, 5-fluoromethylhydantoin, 5-cyclohexyl-hydantoin, 5-(cyclohexylmethyl)hydantoin, 5-(3',4'-dihydroxybenzyl)-hydantoin, 5-(4'-methoxybenzyl)-hydantoin, 5-vinylhydantoin, 5-benzyl-5-ethinylhydantoin, 5,5-trimethylenehydantoin, 1,5-trimethylenehydantoin, 5,5-tetramethylenehydantoin, 5-carboxymethylhydantoin, 5-(carboxamidomethyl)-hydantoin, 5-(2'-carboxyethyl)-hydantoin, 5-(2'-carboxamidoethyl)-hydantoin, or 5-(4'-hydanto-5-yl-2',3'-dithia-butyl)-hydantoin and the α-aminocarboxylic acid salt formed is the sodium salt of glycine, α-aminoisobutyric acid, phenylalanine, alanine, phenylglycine, leucine, 4-hydroxyphenylglycine, tryptophan, 3-fluoroalanine, 2-cyclohexylglycine, 3-cyclohexylalanine, tyrosine, 3,4-dihydroxyphenylalanine, 4-methoxyphenylalanine, 2-amino-vinyl-acetic acid, α-ethinyl-phenylalanine, 1-aminocyclopentane carboxylic acid, proline, pipecolic acid, aspartic acid, glutamic acid or cystine.

8. A process according to claim 1 wherein the materials employed consist of the hydantoin, sodium hydroxide, calcium oxide or hydroxide and water.

9. A process according to claim 3 where $R_3$ is hydrogen or 1 to 4 carbon atom alkyl or $R_2$ and $R_3$ together are an alkylene group having 3 to 5 carbon atoms.

* * * * *